United States Patent [19]

Klahr et al.

[11] 4,349,669
[45] Sep. 14, 1982

[54] PURIFICATION OF ALKYLGLYCOSIDES BY DISTILLATIVE REMOVAL OF UNCONVERTED ALCOHOLS

[75] Inventors: Erhard Klahr; Wolfgang Trieselt, both of Ludwigshafen; Horst Trapp, Plankstadt; Rudi Widder, Leimen, all of Fed. Rep. of Germany

[73] Assignee: BASF Aktiengesellschaft, Ludwigshafen, Fed. Rep. of Germany

[21] Appl. No.: 222,619

[22] Filed: Jan. 5, 1981

[30] Foreign Application Priority Data

Jan. 12, 1980 [DE] Fed. Rep. of Germany ....... 3001064

[51] Int. Cl.$^3$ .............................................. C07H 1/06
[52] U.S. Cl. ..................................... 536/127; 536/124
[58] Field of Search ............................................ 536/4

[56] References Cited

U.S. PATENT DOCUMENTS 2,407,002  9/1946  Griffin ..................................... 536/4
3,375,243  3/1968  Nevin et al. ............................. 536/4
3,378,542  4/1968  O'Boyle .................................. 536/4
3,772,269  11/1973 Lew ....................................... 536/4
4,137,396  1/1979  Louvar et al. ........................... 536/4

FOREIGN PATENT DOCUMENTS 1905523  9/1969  Fed. Rep. of Germany .......... 536/4
2036472  7/1970  Fed. Rep. of Germany .......... 536/4
1072655  6/1967  United Kingdom .................... 536/4

Primary Examiner—Johnnie R. Brown
Attorney, Agent, or Firm—Oblon, Fisher, Spivak, McClelland & Maier

[57] ABSTRACT

A process for purifying $C_8$–$C_{16}$-alkylglycosides which have been obtained by reacting lower alkylglycosides or hydroxyalkylglycosides with $C_8$–$C_{16}$-alcohols in the presence of an acid catalyst, by distillative removal of unconverted $C_8$–$C_{16}$-alcohols, wherein the distillative removal, at least of the last amounts of unconverted alcohols, is carried out in the presence of glycols whose boiling points are at most 10° above, and at most 30° below, those of the alcohols to be removed.

4 Claims, No Drawings

PURIFICATION OF ALKYLGLYCOSIDES BY DISTILLATIVE REMOVAL OF UNCONVERTED ALCOHOLS

The present invention relates to a process for purifying higher alkylglycosides by distillative removal of the higher fatty alcohols which have remained unconverted during the process of preparation.

Higher alkylglycosides, which are used extensively as biologically degradable surfactants, are nowadays prepared almost exclusively by reacting higher alcohols with lower alkylglycosides or hydroxyalkylglycosides in the presence of an acid catalyst, the lower alkylglycosides or hydroxyalkylglycosides having been prepared by reacting monosaccharides, or compounds hydrolyzable to monosaccharides, with lower alcohols.

In the above method, of which numerous embodiments are known, the literature being given below, the reaction in every case results in a mixture of the higher alkylglycoside and the corresponding unconverted alcohol, from which the latter must be removed. Since the boiling points of the higher alcohols, particularly of the fractions with more than 12 carbon atoms, are very high, it was necessary either to carry out the reaction with octyl alcohols to dodecyl alcohols so as to make it possible to remove these, without any problems, under greatly reduced pressure at below 140° C. (at higher temperatures, the sugar residues start to decompose, giving a dark coloration), or an extremely high vacuum had to be applied if higher alcohol fractions, for example industrial mixtures containing $C_{14}$-alkyl or even higher alkyl radicals, still had to be removed.

However, particularly when it is desired to obtain alkylglycosides which give a clear solution in water, the alkylglycosides must be virtually alcohol-free; if they are not, cloudy solutions result.

The preparation of alkylglycosides based on industrial alcohol mixtures containing a proportion of higher ($C_{14}$–$C_{16}$) alcohols is preferred, because of substantial economic advantages, over the preparation using pure alcohols, such as decyl alcohol or dodecyl alcohol.

Since the high vacuum required to remove such mixtures containing higher alcohols also makes the process uneconomical, it was frequently necessary to seek a compromise by leaving the last amounts of alcohol in the mixture or by distilling them off at above 140° C., giving very dark-colored products.

A further obstacle in the way of distillative removal of the higher alcohols is that at up to 140° C. higher alkylglycosides are very viscous materials, which of course makes the removal of the last amounts of alcohol by distillative methods virtually impossible.

It is an object of the present invention to provide a method which makes it possible to purify $C_8$–$C_{16}$-alkylglycosides by distillative removal of even the last amounts of unconverted alcohol.

We have found that this object is achieved by an improved process wherein the distillative removal of at least the last amounts of unconverted alcohols is carried out in the presence of glycols whose boiling points are at most 10° above, and at most 30° below, those of the alcohols to be removed.

The glycols employed act in two ways. First, they act as entraining agents, i.e. they permit the distillative removal of the residual alcohols at <140° C. and under pressures of about 8 millibar, i.e. pressures which are not difficult to realise industrially, and secondly they act as solvents (diluents) for the alkylglycosides, which are therefore also in a low-viscosity form at the distillation temperature.

The alkylglycosides to be purified are derived from reducing monosaccharides, e.g. pentoses or hexoses, or from compounds which can be hydrolyzed to such monosaccharides. Examples of suitable monosaccharides are glucose, mannose, galactose, talose, allose, altrose, idose, arabinose, xylose, ribose and lyxose. Reducing sugars which can be hydrolyzed to the monosaccharides include, for example, oligosaccharides and polysaccharides, such as maltose, lactose, sucrose, raffinose, dextrins, starches, corn syrup and wood sugar.

Glucose, and compounds directly hydrolyzable to glucose, are preferred.

According to the invention, the alkylglycosides are derived from alcohols of 8 to 16 carbon atoms. These include, for example, octanol, decanol, dodecanol, tetradecanol and hexadecanol and their mixtures. Industrial mixtures obtained by oxo synthesis or Ziegler synthesis are preferred, in particular $C_9$–$C_{11}$- and $C_{13}$–$C_{15}$-oxo-alcohols, and $C_{10}$–$C_{12}$-, $C_{12}$–$C_{14}$- and $C_{14}$–$C_{16}$-Ziegler alcohols. Industrial $C_{10}$–$C_{16}$-alcohol mixtures obtained by a Ziegler synthesis are particularly preferred, since they are cheapest.

The glycosides are prepared by prior art methods, for example as described in British Patent No. 1,072,655, by reacting glucose or a lower alkylglucoside with a higher alcohol in the presence of an acidic ion exchanger.

According to German Laid-Open Application DOS No. 1,905,523, glycosides are obtained by, for example, reacting glucose with the higher alcohols in the presence of a lower alcohol or ether-alcohol, in, for example, a sulfuric acid medium. This reaction, again, ultimately involves a trans-acetalization of a lower alkylglycoside with a higher alcohol.

German Published Application DAS No. 2,036,472 discloses that instead of the lower alcohols, lower glycols may be employed; in that case, hydroxyalkylglycosides are formed as intermediates and as constituents of the final mixture.

Finally, it is also possible first to react the sugar exclusively with a lower glycol of 3 to 5 carbon atoms in an acid medium, to isolate the resulting hydroxyalkylglycoside, and then to react this, again in an acid medium, with the desired higher alcohol.

In all these methods, glycosides or glycoside mixtures containing substantial amounts of unconverted higher alcohol are formed.

After neutralizing the acid catalyst, these higher alcohols are removed by distillation. According to the invention, one of the glycols defined in the claim is added when carrying out the distillative removal, either at the start thereof or at least when removing the last amounts of alcohol; in this way, temperatures above 140° C. can be avoided. The preferred procedure is first to subject the glycoside/alcohol mixture, originating from one of the above reactions, to distillation under reduced pressure without an additive, which distillation leaves the higher ($C_{14}$–$C_{16}$) alcohols in the mixture. The glycol is then added and the mixture distilled at about 8 mbar and 135°–140° C., if necessary more than once, until a sample of the residue gives a clear solution in water. The amount of glycol to be added depends on the amount of residual alcohol to be removed and is in general from 5 to 100%, preferably from 10 to 50%, based on the weight of alkylglycoside.

The boiling points of the glycols added should be such that they are not more than 10° above, and not more than 30° below, the boiling point of the residual alcohol which is to be distilled off. The best results are obtained where the differences are <5°.

Examples of such glycols are butane-1,4-diol, diethylene glycol, dipropylene glycol, dibutylene glycol and neopentyl glycol, as well as mixtures of these glycols.

The Example which follows illustrates the invention.

EXAMPLE 70.13 kg of a $C_{10}$–$C_{12}$-alkylglucoside (prepared from glucose and an alcohol cut whose main component was a $C_{10}$–$C_{12}$-cut, but which contained certain amounts of alcohols of up to 16 carbon atoms), which still contained 54% by weight of unconverted alcohol mixture, was first subjected to distillation at 140° C. and 8 mbar to remove the greater part of the excess alcohol. 10 kg of dipropylene glycol were then added, in several portions, to the distillation residue, and in each case the mixture was heated to 140° C. under 8 mbar, causing the last remnants of alcohol to distil off together with the dipropylene glycol.

A parallel experiment carried out, without (glycol) additive, at a pressure of 1.5 mbar and 150° C. yielded a dark brown product which gave a cloudy solution in water.

We claim:

1. In a process for purifying $C_8$–$C_{16}$-alkylglycosides which have been obtained by reacting lower alkylglycosides or hydroxyalkylglycosides with $C_8$–$C_{16}$-alcohols in the presence of an acid catalyst, by distillative removal of unconverted $C_8$–$C_{16}$-alcohols, the improvement that the distillative removal, at least of the last amounts of unconverted alcohols, is carried out in the presence of glycols which are added after substantial termination of the reaction whose boiling points are not more than 10° above, and not more than 30° below, those of the alcohols to be removed.

2. The process of claim 1 wherein said glycols are added at the start of distillative removal.

3. The process of claim 1 wherein said glycols are added to remove the last amounts of uncoverted alcohols.

4. The process of claim 1 wherein dipropylene glycol is added to effect the distillative removal.

* * * * *